United States Patent
Gehling et al.

(10) Patent No.: US 6,518,274 B1
(45) Date of Patent: Feb. 11, 2003

(54) USE OF CYCLOPENTABENZOFURAN-DERIVATIVES FOR COMBATING (NF-κB)-DEPENDENT DISEASES

(75) Inventors: Matthias Gehling, Leichlingen (DE); Jörg Baumgarten, Wuppertal (DE); Axel Kretschmer, Wuppertal (DE); Horst-Peter Antonicek, Bergisch Gladbach (DE); Peter Proksch, Jülich (DE); Bambang Wahyu Nugroho, Bogor (ID); Frank Bohnenstengel, Fürth (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/762,448

(22) PCT Filed: Jul. 29, 1999

(86) PCT No.: PCT/EP99/05426

§ 371 (c)(1),
(2), (4) Date: Apr. 18, 2001

(87) PCT Pub. No.: WO00/07579

PCT Pub. Date: Feb. 17, 2000

(30) Foreign Application Priority Data

Aug. 5, 1998 (DE) .......................................... 198 35 325

(51) Int. Cl.$^7$ ............................. A61P 9/10; A61P 11/06; A61P 7/02; A61K 45/00; C07D 493/12

(52) U.S. Cl. .......................... 514/257; 514/908; 514/66; 514/158; 514/826; 514/825; 514/885; 514/886; 514/824; 424/725; 549/458

(58) Field of Search .................... 424/725; 514/66, 514/158, 826, 825, 885, 886, 908, 257, 824; 549/458

(56) References Cited

U.S. PATENT DOCUMENTS 4,539,414 A  9/1985  King et al. ................. 549/458

FOREIGN PATENT DOCUMENTS

| WO | 9604284 | 2/1996 |
| WO | 9708161 | 6/1997 |

OTHER PUBLICATIONS

Cui, B., Chai, H., Santisuk, T., Reutrakul, V., Farnsworth, N. R., Cordell, G. A., Pezzuto, J. M., and Kinghorn, A. D., "Novel Cytotoxic 1H–Cyclopenta[b]benzofuran Lignans from *Aglaia elliptica*", Tetrahedron 53(52): 17625–17632 (1997).

Davey, A., Schaeffer, M.J., and Taylor, R.J.K., "Synthesis of the Novel Anti–leukemic Tetrahydrocyclopenta[b]benzofuran, Rocaglamide and Related Synthetic Studies", J. Chem. Soc. Perkin Trans. 1, 20: 2657–2666 (1992).

Dumontet, V., Thoison, O., Omobuwajo, O. R., Martin, M.–T., Perromat, G., Chiaroni, A., Riche, C., Pais, M., and Sevenet, T., "New Nitrogenous and Aromatic Derivatives from *Aglaia argentea* and *A. forbesii*", Tetrahedron 52(20): 6931–6942 (1996).

Ko, F.–N., Wu, T.–S., Liou, M.–J., Huang, T.–F., and Teng, C.–M., "PAF antagonism in vitro and in vivo by aglafoline from *Aglaia elliptifolia* Merr", Eur. J. Pharmacol. 218(1): 129–135 (1992).

Lee, S. K., Cui, B., Mehta, R. R., Kinghorn, A. D., and Pezzuto, J. M., "Cytostatic mechanism and antitumor potential of novel 1H–cyclopenta[b]benzofuran lignans isolated from *Aglaia elliptica*", Chem.–Biol. Interact. 115(3): 215–228 (1998).

Nagao, Y., Kim, K., Komaki, Y., Sano, S., Kihara, M., and Shiro, M., "One–pot synthesis of new 1,3–imidazolidines possessing three aryl groups via a 1,3–dipolar cycloaddition reaction", Heterocycles 38(3): 587–593 (1994).

Ohse, T., Ohba, S., Yamamoto, T., Koyano, T., and Umezawa, K., "Cyclopentabenzofuran Lignan Protein Synthesis Inhibitors from *Aglaia odorata*", J. Nat. Prod. 59(7): 650–652 (1996).

Watanabe, T., Kohzuma, S., Takeuchi, T., Otsuka, M., and Umezawa, K., "Total synthesis of (±)–aglaiastatin, a novel bioactive alkaloid", Chem. Commun. 10: 1097–1098 (1998).

Wu, T.–S., Liou, M.–J., Kuoh, C.–S., Teng, C.–M., Nagao, T., and Lee, K.–H., "Cytotoxic and Antiplatelet Aggregation Principles from *Aglaia elliptifolia*", J. Nat. Prod. 60(6): 606–608 (1997).

Database WPI, Section Ch, Week 199913, Derwent Publications Ltd., London, GB; AN 199–148553, JP11012279 A, (ZH Biseibutsu Kagaku Kenkyusho), Jan. 19, 1999.

King, M. L., Chiang, C.–C., Ling, H.–C., Fujita, E., Ochiai, M., and McPhail, A. T., "X–Ray Crystal Structure of Rocaglamide, a Novel Antileukemic 1H–Cyclopenta[b]benzofuran from *Aglaia elliptifolia*", J. Chem. Soc. Commun., pp. 1150–1151 (1982).

Satasook, C., Isman, M. B., and Wiriyachitra, P., Activity of Rocaglamide, an Insecticidal Natural Product, Against the Variegated Cutworm, *Peridroma saucia* (Lepidoptera: Noctuidae), Pestic. Sci., 36: 53–58 (1992).

Loveys, B., and Milborrow, B. V., "Hydroxylation of Methyl Abscisate and the Formation of Three β–D–Glucosides", Phytochemistry, vol. 31(1): 67–72 (1992).

Ishivashi, F., Satasook, C., Isman, M. B., and Towers, G.H.N., "Insecticidal 1H–Cyclopentatetrahydro[b]benzofurans from *Aglaia odorata*", Biochemistry, 32(2): 307–310 (1993).

(List continued on next page.)

*Primary Examiner*—Fredrick Krass
*Assistant Examiner*—Clinton Ostrup
(74) *Attorney, Agent, or Firm*—Connolly Bove Lodge & Hutz LLP

(57) ABSTRACT

The invention relates to the use of cycloventabenzofuran derivatives for the production of a medicament for the treatment of nuclear factor of κB-dependent diseases.

9 Claims, No Drawings

OTHER PUBLICATIONS

Nugroho, B. W., Edrada, R. A., Gussregen, E. B., Wray, V., Witte, L., and Prosksch, P., "Insecticidal Rocaglamide Derivatives from *Aglaia duppereana*", Phytochemistry, 44(8): 1455–1461 (997).

Nugroho, B. W., Gussregen, B., Wray, V., Witte L., Bringmann, G., and Proksch, P., "Insecticidal Rocaglamide Derivatives from *Aglaia elliptica* and *A. harmsiana*", Phytochemistry, 45(8): 1579–1585 (1997).

Gussregen, B., Fuhr, M., Nugroho, B. W., Wray, V., Witte, L., andn Proksch, P., "New Insecticidal Rocaglamide Derivatives from Flowers of *Aglaia odorata*", Z. Naturforsch., C: Biosci., 52(5/6): 339–344 (997).

Barnes, P.J., and Adcock, I. M., "NF–kB: a pivotal role in asthma and a new target for therapy", TIPS, 18: 46–50 (Feb. 1997).

Baeuerle, P.A., and Henkel, T., "Function and Activation of NF–kB in the Immune System", Annu. Rev. Immunol., 12: 141–179 (1994).

Goldfeld, A. E., Doyle, C., and Maniatis, T., "Human Tumor Necrosis Fator α Gene Regulation by Virus and Lipopolysaccharide", Proc. Natl. Acad. Sci., USA, 87: 9769–9773 (Dec. 1990).

Lenardo, M.J., and Baltimore, D., "NF–kB: A Pleiotropic Mediator of Inducible and Tissue–Specific Gene Control", Cell, 58: 227–229 (Jul. 1989).

Oeth, P., Parry, G.C.N., and Mackman, N., "Regulation of the tissue Factor Gene in Human Monocytic Cells. Role of AP–1, NF–kB/Rel, and Sp1 Proteins in Uninduced and Lipopolysaccharide–Induced Expression", Arteriosclerosis, Thormbosis, and Vascular Biology, 17(2): 365–374 (Feb. 1997).

Baldwin Jr., A. S., The NF–kB and IkB Proteins:New Discoveries and Insights, Annu. Rev. Immunol., 14: 649–681 (1996).

Read, M. A., Whtiley, M. Z., Gupta, S., Pierce, J. W., Best, J., Davis, R. J., and Collins, T., "Tumor Necrosis Factor α–Induced E–Selectin Expression is Activated by the Nuclear Factor–kB and c–JUN N–Terminal Kinase/p38 Mitogen–activated Protein Kinase Pathways", J. Biol. Chem., 272(5): 2753–2761 (1997).

USE OF CYCLOPENTABENZOFURAN-DERIVATIVES FOR COMBATING (NF-κB)-DEPENDENT DISEASES

This application is a national stage application filed under 35 U.S.C. 371 of PCT/EP99/05426, filed Jul. 29, 1999.

The invention relates to the use of cyclopentabenzofuran derivatives for the production of a medicament for the therapy of NF-κB-dependent diseases.

Extracts of the plant *Aglaia elliptifolia* exhibit antileukemic properties. The first active compound identified was a dihydrocyclopentabenzofuranol derivative called rocaglamide (J. Chem. Soc., Chem. Commun. 1982, 1150; US 4 539 414). After this, several studies appeared on synthesis experiments which were finally also successful. Only 10 years after the isolation of rocaglamide were its insecticidal properties described (Pestic. Sci. 36 53 (1992); Phytochemistry 32, 67 (1993)) and after that in another species, *Aglaia odorata*, another three derivatives only differing in one substituent were found (Phytochemistry 32, 307 (1993)).

Later, for example, from the species *Aglaia roxburghiana*, the first four fused derivatives of rocaglamide were isolated (WO 96/04 284), then numerous further new derivatives and their pharmacological properties were described (cf., for example, J. Nat. Prod. 59, 650 (1996); Tetrahedron 52 6931 (1996); Phytochemistry 44, 1455 (1997); Phytochemistry 45 1579 (1997); Z. Naturforsch., C: Biosci. 52, Tetrahedron 52, 17625 (1997); B. W. Nugroho, Thesis, Bayer. Julius-Maximilian Univ. Würzburg, 1997, WO 97/08 161 A1, J. Nat. Prod. 61, 1482 (1998), Tetrahedron 53, 17625 (1997).).

An important step in many inflammatory processes is the translocation of the protein "nuclear factor kappa B", in brief NF-κB, into the cell nucleus and the stimulation of the expression of the genes caused thereby, whose products are responsible for inflammatory reactions (Trends Pharmacol. Sci. 18, 46 (1997)). For example, in asthma the nonbeneficial, excessive (non self-limiting) production of these proteins is responsible for the intensification and maintenance of the inflammatory process and the unpleasant to life-threatening symptoms of this disease associated therewith. Because the long-term treatment with glucocorticoids corresponding to the present state of the art is affected by some disadvantages, NF-κB is seen as a compelling target for the development of new anti-inflammatory active compounds against asthma.

It has now been found that the cyclopentabenzofuran derivatives of the formula (I):

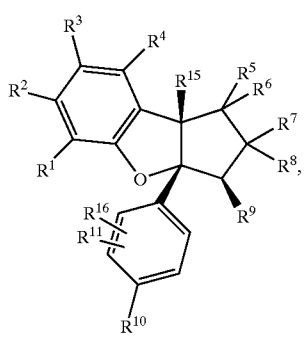

(I)

in which

[A] $R^1$ represents hydrogen,
$R^2$ represents methoxy,
$R^3$ represents hydrogen or
$R^2$ and $R^3$ together represent —OCH$_2$O—,
$R^4$ represents methoxy,
$R^5$ represents hydroxyl, OCHO or acetoxy,
$R^6$ and $R^7$ in each case represent hydrogen or
$R^5$ and $R^6$ together represent oxygen (oxo) or hydroxyimino,
$R^8$ represents —COOR$^{12}$ or —CONR$^{13}$R$^{14}$, in which $R^{12}$ and $R^{13}$ represent hydrogen or methyl and $R^{14}$ represents hydrogen, methyl, 4-hydroxybutyl or 2-tetrahydrofuryl, or $R^8$ represents a radical of the formula:

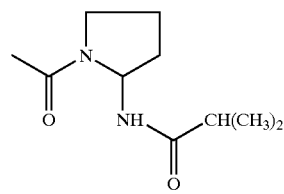

$R^5$ and $R^8$ together represent a group of the formulae (a) or (b):

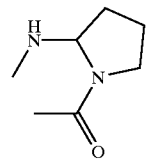

(a)

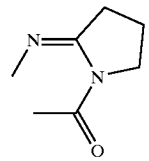

(b)

where the linkage site adjacent to the N atom corresponds to $R^5$ and moreover $R^6$ and $R^7$ together represent a direct bond,
$R^9$ represents phenyl,
$R^{10}$ represents methoxy,
$R^{11}$ represents hydrogen, hydroxyl, 2-methoxy or 2-rhamnosyl, or
$R^{10}$ and $R^{11}$ are adjacent and together represent —OCH$_2$O—, or
$R^{15}$ represents hydroxyl, methoxy or ethoxy,
$R^{16}$ represents hydrogen, hydroxyl or methoxy,
[B] $R^1$, $R^3$ and $R^8$ in each case represent hydrogen,
$R^2$ and $R^4$ in each case represent methoxy,
$R^5$ represents hydroxyl,
$R^6$ and $R^7$ in each case represent hydrogen or
$R^5$ and $R^6$ together represent oxygen (oxo group),
$R^9$ represents phenyl,
$R^{10}$ represents methoxy,
$R^{11}$ represents 2-methoxy or 2-rhanmosyl, or
$R^{10}$ and $R^{11}$ are adjacent and together represent —OCH$_2$O—, are suitable as inhibitors of nuclear factor kappa B (NF-κB)-mediated gene expression for the therapy of pathophysiological processes.

The substances utilizable according to the invention are known from the above-mentioned literature.

Examples of the substances of the formula (I) utilizable according to the invention are the compounds (I-1) to (I-45), which are listed below.

TABLE 1

(I-n)

| No. (n) | $R^2$ | $R^3$ | $R^5$ | $R^6$ | $R^8$ | $R^{10}$ | $R^{11}$ |
|---|---|---|---|---|---|---|---|
| 1 | OCH$_3$ | H | OH | H | CON(CH$_3$)$_2$ | OCH$_3$ | H |
| 2 | OCH$_3$ | H | OH | H | CONHCH$_3$ | OCH$_3$ | H |
| 3 | OCH$_3$ | H | OH | H | CO$_2$CH$_3$ | OCH$_3$ | H |
| 4 | —OCH$_2$O— | | OH | H | CON(CH$_3$)$_2$ | OCH$_3$ | H |
| 5 | —OCH$_2$O— | | OH | H | CON(CH$_3$)$_2$ | OCH$_3$ | OCH$_3$ |
| 6 | OCH$_3$ | H | OH | H | CONH$_2$ | OCH$_3$ | H |
| 7 | OCH$_3$ | H | OH | H | CO$_2$H | OCH$_3$ | H |
| 8 | OCH$_3$ | H | OH | H | CON(CH$_3$)$_2$ | OCH$_3$ | OH |
| 9 | OCH$_3$ | H | OCOCH$_3$ | H | CON(CH$_3$)$_2$ | OCH$_3$ | OH |
| 10 | OCH$_3$ | H | OH | H | CONH(CH$_2$)$_4$OH | OCH$_3$ | H |
| 11 | OCH$_3$ | H | OCOCH$_3$ | H | CONH(CH$_2$)$_4$OH | OCH$_3$ | H |
| 12 | OCH$_3$ | H | OH | H | (tetrahydrofuryl acetamide) | OCH$_3$ | H |
| 13 | OCH$_3$ | H | OH | H | (tetrahydrofuryl acetamide) | OCH$_3$ | H |
| 14 | OCH$_3$ | H | OCOCH$_3$ | H | CONHCH$_3$ | OCH$_3$ | OH |
| 15 | OCH$_3$ | H | OH | H | CONH$_2$ | OCH$_3$ | OH |
| 16 | OCH$_3$ | H | OCOCH$_3$ | H | CO$_2$CH$_3$ | OCH$_3$ | OH |
| 17 | OCH$_3$ | H | OH | H | H | OCH$_3$ | OCH$_3$ |
| 18 | OCH$_3$ | H | OH | H | H | OCH$_3$ | O-rhamnosyl |
| 19 | OCH$_3$ | H | OH | H | CON(CH$_3$)$_2$ | OCH$_3$ | OCH$_3$ |
| 20 | OCH$_3$ | H | OH | H | CONHCH$_3$ | OCH$_3$ | OH |
| 21 | OCH$_3$ | H | OH | H | CONHCH$_3$ | OCH$_3$ | OH |
| 22 | OCH$_3$ | H | =NOH | | CO$_2$CH$_3$ | OCH$_3$ | OCH$_3$ |
| 23 | OCH$_3$ | H | OH | H | CO$_2$CH$_3$ | —OCH$_2$O— | |
| 24 | OCH$_3$ | H | OH | H | H | —OCH$_2$O— | |
| 25 | OCH$_3$ | H | =O | | H | —OCH$_2$O— | |
| 26 | OCH$_3$ | H | OCHO | H | CO$_2$CH$_3$ | —OCH$_2$O— | |

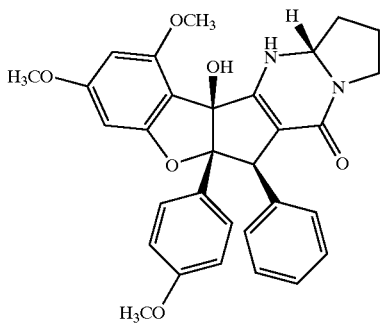

(I-27)

TABLE 1-continued (I-n) [structure with R², R³, OCH₃, R⁵, R⁶, OH, H, R⁸, O, R¹¹, R¹⁰, and phenyl groups]

| No. (n) | R² | R³ | R⁵ | R⁶ | R⁸ | R¹⁰ | R¹¹ |
|---------|----|----|----|----|----|-----|-----|

(I-28) [structure]

(I-29) [structure]

TABLE 2

[structure with numbered positions 1, 3, 5, 7, 2', 5', 4", 5", R⁵, R⁸, R¹¹, R¹⁵, OCH₃, CH₃O, OCH₃, O]

| No. | R⁵ | R⁸ | R¹¹ | R¹⁵ |
|-----|-----|-----|-----|-----|
| 30 | OCOCH₃ | CON(CH₃)₂ | H | OH |
| 31 | OCOCH₃ | CONHCH₃ | H | OH |
| 32 | OCOCH₃ | CONH₂ | H | OH |
| 33 | OH | COOCH₃ | OH | OH |

TABLE 2-continued

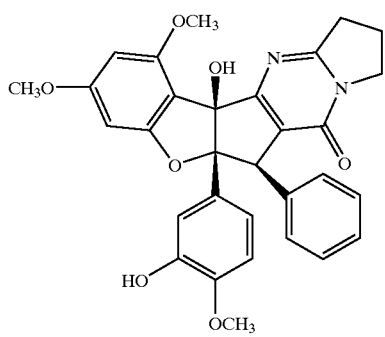

| No. | $R^5$ | $R^8$ | $R^{11}$ | $R^{15}$ |
|---|---|---|---|---|
| 34 | OH | COOCH$_3$ | OCH$_3$ | OH |
| 35 | OCOCH$_3$ | COOCH$_3$ | H | OH |
| 36 | OCHO | COOCH$_3$ | H | OH |
| 37 | OCHO | COOCH$_3$ | OH | OH |

I-38

TABLE 3

| No. | $R^5$ | $R^8$ |
|---|---|---|
| 39* | =O($R^5/R^6$) | H |
| 40 | OCOCH$_3$ | COOCH$_3$ |

*Cui et al., Tetrahedron 53, 17625 (1997)

TABLE 4

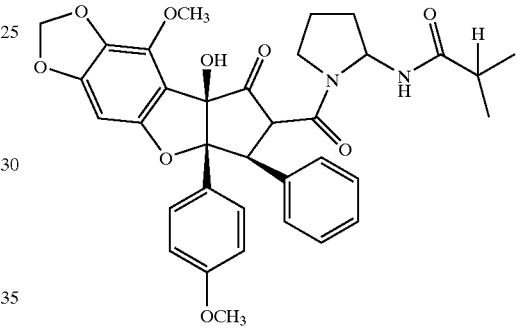

| No. | $R^5$ | $R^8$ | $R^{11}$ | $R^{16}$ |
|---|---|---|---|---|
| 41 | OH | CON(CH$_3$)$_2$ | OCH$_3$ | OH |
| 42 | OH | COOCH$_3$ | H | H |
| 43 | OCOCH$_3$ | COOCH$_3$ | H | H |
| 44* | OH | COOCH$_3$ | OCH$_3$ | H |

*Brader et al., J. Nat. Prod. 61, 1482 (1998).

I-45

Of the above-mentioned substances of the general formula (I), the compounds I-1, I-2, I-3, I-4, I-5, I-6, I-8, I-10, I-12, I-13, I-15, I-19, I-20, I-22, I-26, I-28, I-32, I-33, I-42 are preferred.

The substances utilizable according to the invention are low molecular weight inhibitors which selectively inhibit nuclear factor kappa B (NF-κB)-mediated pathophysiological processes. NF-κB-mediated processes occur in inflammatory diseases, immunological disorders, septic shock, transplant rejection, radiation damage, reperfusion injuries after ischemia, thromboses or in complex, chronic inflammatory disorders such as arteriosclerosis.

The Pharmacological Action of Inhibitors of Nuclear Factor Kappa B

Nuclear factor kappa B (NF-κB) is a dimeric protein complex occurring in many tissue cells and in particular in blood cells. NF-κB takes on a particular role in the control of the expression of genes which have an NF-κB binding sequence (5'-GGGPuNNPyPyCC-3') in their promoter sequence. To this extent, NF-κB is a transcription factor. The physiological activity of NF-κB in the control of gene expression, however, is subject to a regulation principle, in which NF-κB is released from a complex with the protein IκB in order to be translocated as a transcription factor in the cell nucleus of gene activation. The regulation principle for the release of active NF-κB from a complex with the protein IκB is still not known in detail.

Likewise, it is not known how the formation of homodimeric and heterodimeric NF-κB protein complexes takes place. NF-κB acts on gene activation as a dimeric transcription factor. The dimerization can take place under the structurally related transcription factors Rel A, Rel B, c-Rel, p50 or p52, which form a family of transcription factor proteins. In the dimerization of the subunits to the NF-κB, there can also already be a regulation principle for the control of the genes later described in greater detail, which is still not known.

A crucial feature of NF-κB compared to other transcription factors is that NF-κB is a primary transcription factor. Primary transcription factors are already present in the cell in inactive (usually complex-bound) form and are released after an appropriate stimulus in order to be able to display their action very rapidly. Primary transcription factors are not first formed by the activation of the associated gene and subsequent transcription and translation.

This property of NF-κB, the formation of homodimeric or heterodimeric Rel proteins and the formation of an inactive protein complex with an IκB protein, offer very different points of attack for pharmacologically active substances than the points of attack of the de novo biosynthesis of transcription factors. For the sake of completeness, it may be mentioned that the genes for the formation of NF-κB (genes of the Rel family) and the genes for the formation of the IκB proteins (gene family comprising the genes for IκB-α, IκB-β, p105/IκB-γ, p100/IκB-δ, IκB-ε and others) for their part are of course also subject to regulation, which can be points of attack for pharmaceutically active substances. Thus it is known that the expression of the constitutively formed IκB proteins p105 and p100 is increased by stimuli which also activate NF-κB, such as tumour necrosis factor-α (TNF-α) or phorbol myristate acetate (PMA).

A regulation mechanism is described in the literature in which it is shown that the overexpression of IκB binds active NF-κB and thus inactivates it. This also applies if the NF-κB has already entered into a complex with the DNA (P. A. Baeuerle, T. Henkel, Annu. Rev. Immunol. 12, 141–179, 1994). From this it can be concluded that there are a number of specific points of attack in the biochemical function of NF-κB and IκB proteins which should make it possible to inhibit an undesirable, pathophysiological, NF-κB-dependent gene activation selectively.

A chemical compound which selectively inhibits the function of NF-κB or the function of IκB proteins or IκB genes to an increased extent should be able to be used as a pharmaceutical for the suppression of NF-κB-mediated disease processes.

Primarily, NF-κB can promote all pathophysiological processes in which genes are involved which have the NF-κB binding sequence in their promoter. Mainly, these are genes which play a crucial causal role in immunological complications, in inflammatory diseases, autoimnmune disorders, septic shock, transplant rejection, thromboses or else alternatively in chronic inflammatory diseases such as arteriosclerosis, arthritis, rheumatism and psoriasis.

NF-κB binding sequences contain, for example, the promoters of receptors of lymphoid cells (T-cell receptors), of MHCI and MHCII genes, of cell adhesion molecules (ELAM-1, VCAM-1, ICAM-1), of cytokines and growth factors (see also the following table). Furthermore, NF-κB binding sequences are found in the promoters of acute phase proteins (angiotensinogen, complement factors and others).

A chronically increased or acutely overshooting activation of the genes mentioned leads to various pathophysiological processes and syndromes.

The rapid and overshooting production of cytokines of the inflammatory reaction (TNFα, interleukin-2, interleukin-6, interleukin-8 and others) and of the adhesion molecules (ELAM-1, ICAM-1, VCAM-1) in leukocytes, in particular in macrophages and also in endothelial cells, is a causal feature of processes which often run a fatal course in the case of septic shock; or in the case of radiation damage and in the case of transplant rejection often leads to considerable complications. Inhibitors which prevent the NF-κB-mediated gene expression intervene very early in some diseases in the expression of pathophysiological changes and can therefore be a very effective therapeutic principle. An example is also NF-κB inhibitors for diseases which are to be attributed to an overexpression of acute-phase proteins. An undesirable overexpression of acute-phase proteins can cause a complex general reaction in which tissue damage of very different types, fever and local symptoms such as inflammation and necroses can occur. Usually, the blood picture is changed. NF-κB strongly induces, for example, the serum amyloid A precursor protein in the liver in the course of induction of acute-phase proteins.

For example, the NF-κB-mediated gene expression of the interleukin-2-(Il-2) gene can be inhibited.

Interleukin-2 is a cytokine which plays a central role in various inflammatory processes, inter alia, as a hematopoietic growth factor (Annu. Rev. Immunol. 1994, 12: 141–79). The promoter of the interleukin-2 gene is NF-κB dependent. An inhibitor of NF-κB stimulation thus opens up the possibility of preventing overshooting of Il-2 production and thus of treating inflammatory processes.

In the case of other syndromes such as tissue damage after reperfusion or cirrhosis of the liver, inhibitors of NF-κB-mediated gene expression can likewise represent an important therapeutic advance. There is evidence that NF-κB-controlled genes are induced as a result of oxidation reactions which lead to oxidative stress after reperfusion of ischemic tissue. In this way, an overexpression of cytokines and cell adhesion molecules in the ischemic tissue causes excessive recruitment of infiltrating alymphocytes. The recruited lymphocytes contribute causally to the tissue damage.

The involvement of NF-κB-controlled gene expression is evident in a number of neurodegenerative disorders. In particular in the case of nervous diseases in which the redox state of cells of the neuronal tissue is disturbed, a therapeutic benefit is ascribed to the selective inhibition of genes having an NF-κB binding sequence. A disturbed redox state of neuronal cells is assumed in the case of ainyotropic lateral sclerosis and in Down's syndrome.

It is known that NF-κB is a frequently encountered transcription factor in neuronal tissue and that NF-κB is a redox potential-controlled transcription factor in the brain (P. A. Bauerle, T. Henkel, Annu. Rev. Immunol. 12, 141–179, 1994). A formulation of the genes which are induced by NF-κB is shown in Table 2.

TABLE 2

Genes which are induced by NF-κB (P.A. Bauerle, T. Henkel, Annu. Rev. Immunol. 12 141–179, 1994)

| | |
|---|---|
| Immunoreceptors | Immunoglobulin κ light chain |
| | T cell receptor β |
| | T cell receptor α chain (human) |
| | Major histocompatibility complex class I (H-2K) |
| | $\beta_2$-microglobulin |
| | Invariant chain I |
| | Tissue factor-1 |
| Cell adhesion molecules | Endothelial leukocyte adhesion molecule 1 (ELAM-1) |
| | Vascular cell adhesion molecule 1 |

TABLE 2-continued

Genes which are induced by NF-κB (P.A. Bauerle, T. Henkel, Annu. Rev. Immunol. 12 141–179, 1994)

| | |
|---|---|
| | (VCAM-1) |
| | Intercellular cell adhesion molecule 1 (ICAM-1)* |
| Cytokines and growth factors | β-Interferon |
| | Granulocyte/macrophage colony-stimulating factor (GM-CSF) |
| | Granulocyte colony-stimulating factor (G-CSF) |
| | Macrophage colony-stimulating actor (M-CSF) |
| | Melanoma growth stimulating activity (groα-γ/MGSA) |
| | Interleukin-2 |
| | Interleukin-6 |
| | Interleukin-8 |
| | TNFα |
| | Lymphotoxin (TNF-β) |
| | Proenkephalin |
| | MPC-1/JE* |
| Acute-phase proteins | Angiotensinogen |
| | Serum amyloid A precursor |
| | Complement factor B |
| | Complement factor c4 |
| | Urokinase-type plasminogen activator* |

*The binding of NF-κB to the promoter of the gene mentioned has still not been conclusively demonstrated experimentally.

In addition to the already mentioned genes, whose activity is controlled by the release of NF-κB and which particularly play a role in inflammatory processes, septic shock and transplant rejection, NF-κB-controlled genes in viruses may also be mentioned and those which produce oncogenic cellular changes (oncogenes such as c-myc, c-rel, melanoma growth stimulating activity MGSA). In these genes too, selective inhibition of NF-κB binding is a promising, therapeutically utilizable concept. The gene expression of lymphotrophic viruses such as HIV, HTLV and Epstein-Barr virus is activated either directly or by NF-κB or NF-κB is induced in the infected host cell, which is favourable to virus replication. In addition, HIV has an NF-κB-positive action on gene expression in the cytomegalovirus (CMV) and adenovirus. Antiviral effects with NF-κB inhibitors are conceivable here too.

The use of the substances which can be used according to the invention is evident from the following examples.

USE EXAMPLES

Example A

Inhibition of the NF-κB-mediated Gene Expression of the Tumour Necrosis Factor-α(TNFα) Gene in Human Monocytes The promoter of the human TNFα gene contains 3 NF-κB binding sequences which are designated as k1, k2 and k3. The NF-κB binding sequences are found in the promoter of the TNFα gene in the nucleotide positions k1=−587 to −577, k2=−210 to −202 and k3=−98 to −87 and these DNA sequences specifically bind NF-κB (A. E. Goldfield et al., Proc. Natl. Acad. Scri. USA 87, 9769–9773, 1990). Lipopolysaccharide or phorbol esters (such as phorbol myristate acetate) induce NFκB release (M. J. Lenardo et al., Cell 58, 227–229, 1989).

The following biological test is therefore carried out to detect the inhibition of the NF-κB-mediated TNFα gene expression by the substances described here.

Mononuclear cells from donor blood are isolated using Vacutainer CPT™ tubes (Becton Dickinson and Company, Franklin Lakes, N.J. 07417-1885), according to the instructions of the manufacturer. The Vacutainer CPT tubes contain 1.0 ml of phosphate-buffered saline with 120 USP units of sodium heparin above 3.0 g of a polyester gel which is covered with a layer of 2.0 ml of a Ficoll solution. After the centrifugation of the donor blood, the monocytes are taken from a zone above the polyester gel and inoculated at a cell density of $250 \times 10^5$ cells per well into 96-well microtiter plates for cell culture.

The cells are incubated for 4–6 hours in RPMI-1640 medium (Gibco BRL, Life Technologies GmbH, Dieselstr. 5, 76344 Eggenstein). The culture supernatant is then aspirated, RPMI-1640 medium is added again and the substances to be tested are added in concentrations customarily between 0 $\mu$M (negative control) and 20 $\mu$M.

Bacterial lipopolysaccharide (LPS), Sigma-Aldrich Chemie GmbH, Grünwalder Weg 30, 82039 Deisenhofen, Order No.: L 4391, is then added in a concentration of 125 ng/ml for the stimulation of the NF-κB-mediated TNFα gene expression. After a further incubation of 18 hours at 37° C. in a 5% $CO_2$ atmosphere, culture supernatant is removed from the microtiter plates and the TNFα content therein is determined quantitatively using commercially available enzyme-bound immunosorbent assays (ELISA).

TNFα ELISA for concentration determination are marketed, for example, by Sigma-Aldrich Chemie GmbH, Grünwalder Weg 30, 82039 Deisenhofen under the name Human TNFα ELISA Kit, Order No.: CKH-200A. According to the use instructions of the manufacturer, the concentration of the TNFα formed in the culture supernatant of the monocyte culture is determined quantitatively after LPS stimulation with and without inhibitor substance.

The results of the TNFα-concentration determination are plotted against one another in an x/y graph. The graph of the y coordinates (TNFα concentration in the culture supernatant) and of the x coordinates (concentration of the inhibitor employed) enables the inhibition of the NF-κB-mediated TNFα synthesis to be read off as a function of the concentration of the inhibitor substance. In this way, it is possible to read off from the graph that active compound concentration of the added inhibitor which inhibits, for example, TNFα synthesis by 50%. This active compound concentration which produces a 50% inhibition is called the effective inhibitor concentration for 50% inhibition ($IC_{50}$).

For example, the concentrations of the half-maximal TNFα synthesis inhibition ($IC_{50}$) of the compound I-2 (from Table 1) are 0.3 $\mu$M, in the case of compound I-15 1.0 $\mu$M and in the case of compound I-21 0.5 $\mu$M. The compounds are thus potent inhibitors of NF-κB-mediated TNFα synthesis.

Example B

Inhibition of the NF-κB-mediated Gene Expression of the Human Tissue Factor Gene in Monocytes Tissue factor is a membrane protein which is the primary initiator of the blood coagulation cascade and takes on a key function in cardiovascular diseases such as unstable angina pectoris, acute implications after plaque rupture, vascular occlusions of varying etiology, arteriosclerotic processes and other illnesses such as septic shock or cancer. The tissue factor gene is induced by NF-κB activation, in particular in monocytes and endothelial cells. The promoter of the human tissue factor gene contains an NF-κB binding site which contributes crucially to the activation of the promoter (P. Oeth et al. Arteriosclerosis, Thrombosis, and Vascular Biology 17, 365–374, 1997).

Therefore, for the further detection of the inhibition of the NFκB-mediated gene expression by the inhibitors according to the invention, the following biological test was carried out:

The promoter fragment of the human tissue factor gene which contains the NF-κB binding sequence was cloned with oligonucleotide primers of the sequence 5'-TCC CTC GAG ATC TCC CAG AGG CAA ACT GCC AGA T-3' (5' primer of position -925) and 5'-TCC TCG AGC CAT GGC TAC CAG TTG GGC GGC GAG ATC-3' (3' primer containing the ATG start codon of the coding sequence of the tissue factor gene) by means of the polymerase chain reaction (PCR) and fused by means of an NcoI/XhoI cloning with the luciferase start codon in the plasmid pGL3-basic vector (Promega Corp. 2800 Woods Hollow Road, Madison, Wis. 53711-5399 USA). By means of this, the expression of the luciferase in the recombinant plasmid thus resulting is regulated by the human tissue factor promoter. This expression construct was subjected to DNA sequencing analysis and transfected into the monocyte cell line RAW 264.7 (American Type Culture Collection 12301 Parklane Drive, Rockville, Md. 20852, USA). The transfection, selection and clone analysis was carried out by standard methods, such as have been described (see Transfection of Mammalian Cells in Culture, L. G. Davis et al. Basic Methods in Molecular Biology, Elsevier Sci. Publishing Co., New York 1986). After the selection of RAW 8 clones which had integrated the expression construct stably in the genome, one of these transfectants, called RAW-A3, was selected for the testing of the inhibitors.

Test Procedure:

$10^6$ RAW-A3 cells are inoculated into each depression in 12-well microtiter plates. The serum concentration is lowered stepwise in the course of three days in the RPMI medium from 10% fetal calf serum to 0.5% and 0.1% serum content in order to lower the serum-dependent tissue factor promoter activation to a minimum. After culture in medium containing 0.1% serum for 24 hours, the NF-κB inhibitor is added and serum is then added up to a concentration of 15% in the medium for promoter induction.

After a further 6 hours, the culture supernatant is aspirated and the cells are processed for the measurement of the luciferase activity according to the procedure of the "Luciferase Assay System" (Technical Bulletin of Promega, 2800 Woods Hollow Road, Madison, Wis. 53711-5399 USA, Products E4030, E1483, E1501). The cell lyzate is incubated with the luciferase assay substrate and measured in a luminometer to measure the emitted light. In a plot in an x/y graph with the light emitted in each case (indicated in relative light units) as y coordinates and the inhibitor concentrations as x coordinates, a graph for f(x) results in which the half-maximal y value of an inhibitor concentration x is to be assigned which corresponds to the inhibitor concentration $IC_{50}$ in this test.

For example, the $IC_{50}$-value of the compound I-2 (from Table 1) is 0.4 μM and the compound I-21 4.0 μM. The NF-κB-mediated expression of the luciferase by the inhibitors according to the invention with a concentration in the lower micromolar or in the submicromolar range points to the high activity of the inhibition of an NF-κB-mediated gene expression.

Example C

Inhibition of the NF-κB-mediated Gene Expression of the Tumour Necrosis Factor-α (TNFα) Gene in Human Monocytes as a Function of Three Different TNFα Synthesis Stimuli The NF-κB-mediated induction of TNFα-synthesis is independent of the different stimuli which are employed by LPS, opsonized zymosan or phorbol myristate acetate (PMA) for the activation of the TNFα promoter (A. Baldwin, Annual Rev. Immunology 14, 649, 1996). Therefore the use of the inhibitors according to the invention should also lead to a comparatively strong inhibition of TNFα synthesis independently of the nature of the stimulation of the TNFα synthesis.

The tests for this detection of the stimulus-independent inhibition of TNFα synthesis were carried out by the type of test procedure exactly as is described in Example A with the difference that in addition to LPS as a stimulus, cell culture batches were also stimulated with 100 nM PMA or with 100 μg/ml of opsonized zymosan. Zymosan and phorbol myristate acetate (PMA) can be ordered from Sigma, Gr ünwalder Weg 30, 82041 Deisenhofen, Germany under Order Nos. Z4250 and P8139. Zymosan is opsonized in human serum.

Independently of the stimulus, the NF-κB-inhibitors according to the invention inhibit the TNFα synthesis in human monocytes as was shown in Example A in a comparative manner with $IC_{50}$ values in the submicromolar range. Thus for compound I-2 the $IC_{50}$ value after PMA stimulus is 0.4 μM and after zymosan stimulus 0.4 μM.

Example D

Inhibition of the NF-κB-mediated Gene Expression of the Adhesion Protein ELAM-1 to Human Umbilical Cord Endothelial Cells (HUVEC)

The recruitment of leukocytes from the blood circulation into the extravascular space is essential in inflammatory responses and in the repair of tissue damage. The process of leukocyte infiltration comprises a number of steps connected in series. The initial interaction between leukocytes and the endothelium of the blood vessels is mediated by TNF and I-1-1-dependent expression of the adhesion protein ELAM-1 on the endothelium. It mediates the so-called rolling of the leukocytes along the blood vessel wall. The transcriptional regulation of the ELAM-1 expression is dependent both on the nuclear factor-κB (NF-κB) activation and binding to the ELAM-1 promoter and on the "AP-1 binding site. M A. Read et al., J. Biol. Chem. Vol. 272, 2753–2761, (1997).

The influence of compound I-2 on the expression of ELAM-1 was checked in two different test batches. In one functional batch, the adhesion of human neutrophils to TNF-α-stimulated HEVEC cells was measured. The expression of ELAM-1 on the surface of the HEVECs was determined using a fluorescence-labeled ELAM-1 specific monoclonal antibody by means of FACS (cell sorting) analysis.
Experimental Procedure: ELAM-dependent Neutrophil Adhesion to Endothial Cells The neutrophils were isolated from human blood (100 ml). To this end, 3.5 ml of Polyprep was introduced into a centrifuge bucket and carefully coated with 5 ml of blood. After centrifuging at 2 100 $min^{-1}$ for 30 minutes, the neutrophil band in the center of the centrifuge bucket was aspirated. After 1:2 dilutions in Clonetics endothelial cell basal medium (EBM), the neutrophils were again centrifuged at 1000 $min^{-1}$ for 20 minutes and then made up to a cell concentration of $10^6$ cells/ml.

The umbilical cord endothelial cells were grown to confluence in EBM+10% FCS in 96 well microtiter plates. At the start of the experiment, the medium was replaced by EBM without FCS and the experimental substances then employed. After 20 minutes, the HUVECs were stimulated using 10 nM TNF-α. After incubation for 4 hours replacement was carried out by 200 µl/well of the neutrophil suspension. The neutrophils had been labeled with a 25 µM BCECP fluorescent dye solution for 20 minutes beforehand. After incubation for 30 minutes, the BCECP neutrophil solution was stripped off with excess neutrophils and replaced by 200 µl/well of 0.5% strength NaOH solution. The fluorescence of the adherent neutrophils was then measured in a fluorescence photometer.

Both the adhesion of the neutrophils to TNF-α-stimulated HUVECs, and the expression of ELAM-1 on the cell surface were inhibited to 50% by the compounds. The maximum inhibition of cell adhesion was determined at 10 µM for compound I-2. The maximum 50% inhibition of the ELAM-1 expression is in good agreement with the simultaneously NF-κB and AP-1-dependent regulation of the ELAM-1 promoter.

Experimental Procedure Quantitative Measurement of the TNF-induced Expression of ELAM-1 in HUVECs Umbilical cord endothelial cells (HUVEC) were cultured as described above and incubated for 4 hours in the presence or absence of test substances in the presence or absence of 10 ng/ml of TNF. The cells were dissolved out of the microtiter plates by incubation with 5 mM EDTA in PBS, centrifuged at 1000 min$^{-1}$ for 5 minutes, and incubated at RT in 100 µl of PBS plus 1% bovine serum albumin (BSA, Sigma-Aldrich GmbH, Order No. A7906) in an anti-ELAM 1 antibody (monoclonal antibody, Becton and Dickinson, Erembodegem, Belgium, Order No. 550 023, 30 µg/ml). After 15 minutes, the cells were again centrifuged, the supernatant was discarded and the cells were washed in PBS plus 1% BSA. After centrifugation again, the cell pellet obtained was incubated for a duration of 15 minutes in PBS plus 1% BSA and a goat-anti-mouse antibody (Dianova, Raboisen 5, Hamburg; Order No. 115-096–062;30 µg/ml). After centrifuging and washing again, the cells were taken up in 1 ml of PBS plus 1% BSA and measured at 488 nm in a flow cytometer (Becton and Dickinson). The intensity of the fluorescence as a function of bound anti-ELAM-1 antibody per cell is measured by this process. 5000 cells were measured for each value.

After incubation with anti-ELAM-1 antibodies, HUVECs which had been stimulated with TNF for 4 hours showed markedly stronger fluorescence signals than cells which, on the other hand, had not been incubated with TNF. The compound I-2 was able to inhibit this induced expression of ELAM-1 in a concentration range between 0.05 µM and 5 µM significantly, but the expression of ELAM-1 was completely inhibited at none of the concentrations investigated.

Example E

Inhibition of Interleukin-2 Synthesis

For the testing of the inhibitory action of cyclopentabenzene derivatives on interleukin-2 synthesis, a receptor gene cell line was used which contains the interleukin-2 promoter coupled to the luciferase gene. The promoter contains the DNA sequence from −480 to +4. The vector employed is pGL3; the starting cell line in which the total construct has been stably transfected is SS-1. The culture medium for this cell line was RPMI 1640 (Gibco, Rockille). It additionally contained: 100 µg/ml of streptomycin, 100 U/ml of penicillin, 2 mM L-glutamine, 10% heat-inactivated FBS and 800 µg/ml of G418 sulfate.

Test Procedure

The reporter gene test cell line was inoculated into 96-well plates to 1×10$^6$ cells per well in Phenol Red-free RPMI with the additives and incubated at 37° C. in an atmosphere of 5% CO$_2$, 95% air with phorbol 12-myristate 13-acetate (PMA; 5 ng/ml) and ionomycin (10 M; 0.4 µg/ml) for 24 hours. The test substances were added simultaneously with PMA.

Measurement of the Luciferase Activity:

For the generation of the luminescence, LucLite™ solution (Packard, Meriden, Conn.) was added to a concentration of 100 µl/well and the luminescence was measured in a luminometer (Luminoskan, Labsystems) immediately after addition.

What is claimed is:

1. A method of treating a nuclear factor κB-dependent disease selected from the group consisting of immunological disorders, septic shock, transplant rejection, radiation damage, reperfusion injuries after ischemia, arteriosclerosis and neurodegenerative diseases, comprising administering to a mammal in need of such treatment an effective amount of a cyclopentabenzofuran derivative of the formula (I):

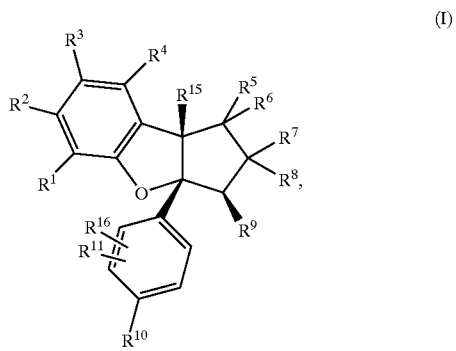

(I)

in which

[A] R$^1$ represents hydrogen,
R$^2$ represents methoxy,
R$^3$ represents hydrogen or
R$^2$ and R$^3$ together represent —OCH$_2$O—,
R$^4$ represents methoxy,
R$^5$ represents hydroxyl, OCHO or acetoxy,
R$^6$ and R$^7$ in each case represent hydrogen or
R$^5$ and R$^6$ together represent oxygen (oxo) or hydroxyimino,
R$^8$ represents —COOR$^{12}$ or —CONR$^{13}$R$^{14}$, in which
R$^{12}$ and R$^{13}$ represent hydrogen or methyl and
R$^{14}$ represents hydrogen, methyl, 4-hydroxybutyl or 2-tetrahydrofuryl, or R$^8$ represents a radical of the formula:

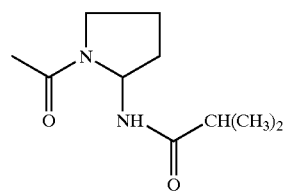

R$^5$ and R$^8$ together represent a group of the formulae (a) or (b):

(a) 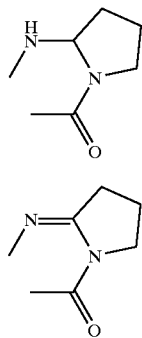

(b) 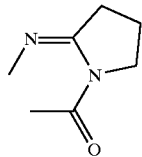

where the linkage site adjacent to the N atom corresponds to $R^5$ and moreover $R^6$ and $R^7$ together represent a direct bond, $R^9$ represents phenyl, $R^{10}$ represents methoxy, R11 represents hydrogen, hydroxyl, methoxy or 2-rhamnosyl, or $R^{10}$ and $R^{11}$ are adjacent and together represent —OCH$_2$O—, or $R^{15}$ represents hydroxyl, methoxy or ethoxy, R16 represents hydrogen, hydroxyl or methoxy,

[B] $R^1$, $R^3$ and $R^8$ in each case represent hydrogen, $R^2$ and $R^4$ in each case represent methoxy, $R^5$ represents hydroxyl, $R^6$ and $R^7$ in each case represent hydrogen or $R^5$ and $R^6$ together represent oxygen (oxo group), $R^9$ represents phenyl, $R^{10}$ represents methoxy, $R^{11}$ represents 2-methoxy or 2-rhamnosyl, or $R^{10}$ and $R^{11}$ are adjacent and together represent —OCH$_2$O—, $R^{15}$ represents hydroxyl, methoxy or ethoxy, $R^{16}$ represents hydrogen, hydroxyl or methoxy.

2. The method of claim 1 wherein said cyclopentabenzofuran derivative is a compound of formula I wherein $R^{15}$ is hydroxyl and $R^{16}$ is hydrogen.

3. The method of claim 1 wherein said nuclear factor-κB-dependent disease is an immunological disorder.

4. The method of claim 1 wherein said nuclear factor-κB-dependent disease is septic shock.

5. The method of claim 1 wherein said nuclear factor-κB-dependent disease is transplant rejection.

6. The method of claim 1 wherein said nuclear factor-κB-dependent disease is radiation damage.

7. The method of claim 1 wherein said nuclear factor-κB-dependent disease is reperfusion injury after ischemia.

8. The method of claim 1 wherein said nuclear factor-κB-dependent disease arteiosclerosis.

9. The method of claim 1 wherein said nuclear factor-κB-dependent disease is a neurodegenerative disease.

* * * * *

UNITED STATES PATENT AND TRADEMARK OFFICE
CERTIFICATE OF CORRECTION

PATENT NO.   : 6,518,274 B1                                                        Page 1 of 1
DATED        : February 11, 2003
INVENTOR(S)  : Matthias Gehling et al.

It is certified that error appears in the above-identified patent and that said Letters Patent is hereby corrected as shown below:

Column 18,
Line 12, after "formula I" insert -- [B] --.
Line 26, after "disease" please replace "arteiosclerosis" with -- is arteriosclerosis --.

Signed and Sealed this

Twenty-fourth Day of June, 2003

JAMES E. ROGAN
*Director of the United States Patent and Trademark Office*